United States Patent [19]

Good

[11] 4,341,799

[45] Jul. 27, 1982

[54] LOTION AND METHOD FOR CLEANSING AND CONDITIONING THE SKIN THEREWITH

[76] Inventor: Allen H. Good, 149 Kent Place Blvd., Summit, N.J. 07901

[21] Appl. No.: 220,367

[22] Filed: Dec. 29, 1980

[51] Int. Cl.$^3$ .......................... A61K 7/00; A61K 7/50
[52] U.S. Cl. ...................................... 424/365; 424/70; 424/358
[58] Field of Search ........................... 424/70, 358–365

[56] References Cited

U.S. PATENT DOCUMENTS

| | | | |
|---|---|---|---|
| 1,979,385 | 11/1934 | Harvy | 252/551 X |
| 3,548,056 | 12/1970 | Eigen | 252/551 X |
| 3,634,265 | 1/1972 | Merritt | 252/551 X |
| 4,128,631 | 12/1978 | Lundmark | 424/70 |
| 4,130,497 | 12/1978 | Oneto | 424/70 X |

FOREIGN PATENT DOCUMENTS 1018385  1/1966  United Kingdom ................ 424/365

OTHER PUBLICATIONS

Schimmel Briefs, Schimmel & Co., N.Y. No. 299, Feb. 1960, 1 p.; No. 381, Dec., 1966, 1 p.
Balsam & Sagarin, Cos. Sci & Tech, Wiley-Intersci, NY vol. I, 2nd Ed. 1972 pp. 1–3, 12–17, 20, 21, 44–48, 54–58, 62, 63, 70–77.

*Primary Examiner*—Anna P. Fagelson

[57] ABSTRACT

A non-greasy skin lotion emulsion composition having a cleansing action on the skin and adapted for use with water to break the emulsion and deposit a moisturizer on the skin to coat and condition the skin, comprising a mineral oil, water, a $C_{12}$–$C_{15}$ alkali metal alcohol ether sulfate, and a long chain fatty acid; having a pH in the range 6.5 to 7.5; and optionally containing thickening agents, preservatives, fragrances, and other conventional skin lotion additives.

10 Claims, No Drawings

LOTION AND METHOD FOR CLEANSING AND CONDITIONING THE SKIN THEREWITH

This invention relates to non-greasy skin lotions having a unique combination of skin cleansing action plus a residual ski conditioning activity after the lotion is rinsed from the skin with water, and to methods of using the lotions.

Skin lotions are, of course, well known to the art and are in daily use by consumers. However, commercially available skin lotions are formulated to be applied to the skin without rinsing of the lotion from the skin. Also, such lotions do not usually contain ingredients designed to effectively cleanse the skin. In fact, if non-greasy prior art skin lotions are rinsed from the skin, almost complete removal of the lotion will result, leaving no appreciable skin conditioning activity in their wake, and no effective removal of dirt from the skin will have occurred. With respect to greasy prior art skin lotions, rinsing will remove little if any of the lotion and none of the dirt.

Skin cleansing compositions are also well known to the art, and such compositions, unless of the so-called waterless hand cleaner type, are specially designed to be used with, and removed by, the addition of water. However, upon rinsing such cleansing compositions from the skin, followed by drying of the skin, little or no skin conditioning effect remains. In fact, most cleansing compositions tend to dry and irritate the skin, rather than condition it.

As stated above, the present lotion compositions provide a combination of cleansing action with significant residual skin conditioning effects after the skin containing the lotion is rinsed with water and the skin is dryed. These lotion compositions are non-greasy emulsions, formulated so that the emulsion breaks when the skin is rinsed with water. When the emulsion breaks, two beneficial effects occur: (a) dissolved and emulsified dirt from the skin remains in the acqueous phase and is rinsed from the skin, and (b) mineral oil is released from the emulsion, coating the skin in sufficient quantities so that even after the skin is dryed, enough mineral oil remains on the skin to moisturize and soften the skin, without, however, imparting a slippery or oily feel to the skin.

The novel skin lotions of the present invention comprise:

(a) from about 55 to about 80, preferably from about 65 to 75, percent by weight of water;

(b) from about 1.1 to about 5.5, preferably from about 1.8 to about 3.0, percent by weight of one or more $C_{10}$ to $C_{18}$ saturated or monoolefinic fatty acids;

(c) from about 15 to about 30, preferably from about 22 to about 25, percent by weight of a mineral oil having a viscosity in the range of from about 60 to about 350 SSU at 100° F.;

(d) from about 0.4 to about 2.0, preferably from about 1.0 to about 1.4 percent, by weight of one or more $C_{12}$-$C_{15}$ alkali metal alcohol ether sulfates; and (e) an alkaline neutralizing agent which is added to the above composition in amounts sufficient to bring the pH of the composition into the range 6.5 to 7.5, preferably about 6.8 to 7.2.

In addition to the above ingredients, the lotion compositions of the invention may contain, optionally but preferably, a small quantity, e.g., from about 0.01% to about 3.0% by weight, of a cosmetically acceptable thickening agent. Such thickening agents are well known to the art and are commercially available from several manufacturers. Among those which may be used include xanthan gum, marketed by Kelco, division of Merck & Co., Inc., under the trademark KELTROL, which is a high molecular weight, linear exocellular material prepared by the action of bacteria of the genus Xanthomonas on carbohydrates, described in greater detail in U.S. Pat. No. 3,020,206; sodium carboxymethyl cellulose; carboxymethylene polymer having a molecular weight of from 1 to 4 million; hydroxyethyl cellulose; guar gum; and gum tragacanth. Xanthan gum, in amounts of from about 0.5 to about 0.8 percent by weight, is preferred. The thickening agent, while not essential, does impart a desirable consistency and "feel" to the composition.

In addition, small quantities of other ingredients may be added to the lotion compositions, such as preservatives (antibacterial and/or antifungal agents, e.g. DOWICIL 200, the cis isomer of 1-(3-chloroally)-3,5,7-triaza-1-azoniaadamantane chloride); antioxidants, e.g. methyl and propyl parabens; fragrances; and other conventional skin lotion additives.

The combination of a $C_{10}$ to $C_{18}$ saturated or monoolefinic fatty acid with a $C_{12}$-$C_{15}$ alkali metal alcohol ether sulfate at a pH of 6.5 to 7.5 in the above composition containing water and mineral oil, all in the percentages given above, results in a very stable lotion emulsion prior to use, which, however, is readily broken when excess water is used to rinse the skin to which the lotion emulsion has been applied.

Examples of the $C_{10}$ to $C_{18}$ saturated or monoolefinic fatty acids that can be employed in the compositions of the invention include capric acid, lauric acid, myristic acid, pentadecanoic acid, palmetic acid, margaric acid, stearic acid, and oleic acid. Mixtures of these acids can be employed. A combination of double press USP stearic acid and coconut fatty acids has been found to be particularly convenient. Double press USP stearic acid is composed of approximately equal quantities of palmitic and stearic acids together with small quantities of $C_{14}$ to $C_{17}$ fatty acids. Coconut fatty acids comprise about 50% by weight lauric acid, 18% by weight myristic acid, and smaller quantities of other fatty acids.

The $C_{12}$-$C_{15}$ alkali metal alcohol ether sulfate used in the compositions of the invention is preferably the sodium salt of a mixture of $C_{12}$ to $C_{15}$ alcohol ether sulfates (sodium myreth sulfate) by Henkel, Inc. under the tradenames AVIROL - BOD 153 and SULFOTEX LMSE. This mixture of sulfates has the formula $C_{12}$-$C_{15}H_{25-31}O(CH_2CH_2O)_2CH_2CH_2OSO_3^-Na^+$ wherein the $C_{12}$-$C_{15}$ alkyl groups are predominantly linear alkyl groups.

The alkaline neutralizing agent used to adjust the pH of the lotion compositions into the range of pH 6.5 to 7.5 can be any alkaline neutralizing agent having a cosmetically acceptable cation, such as KOH, NaOH, and mono-,di-, and triethanolamines. However, when an alkaline neutralizing agent is used which is also an effective emulsifying agent, e.g., the ethanolamines, it is important to use such neutralizing agents in the compositions of the invention in very small quantities only, for example, less than 0.5% by weight, since use of larger quantities will results in an emulsion which will not be readily broken upon rinsing with water. Accordingly, it is preferreed to use either KOH or NaOH, preferably KOH, to adjust the pH of the present compositions into the desired range.

Prior art compositions include those disclosed in the following U.S. Patents:

| NO. | Patent Date | Title | Inventor |
|---|---|---|---|
| 1,979,385 | Nov. 6, 1934 | Cosmetic Preparation | Norman D. Harvey, Jr. |
| 3,548,056 | Dec. 15, 1970 | Skin Protecting Composition Containing a Water-Soluble Partially Degraded Protein | Edward Eigen & Sidney Weiss |
| 3,634,265 | Jan. 11, 1972 | Skin Cleaner Requiring No Addition of Water for Cleaning Therewith | George J. Merritt |

The emulsified cream compositions of U.S. Pat. No. 1,979,385 do not contain the combination of fatty acid and alkali metal alcohol ether sulfate compound required in the present composition. In fact, the only composition designed as a cleansing cream, that set forth in Example 2 of this patent, states that the composition is specifically formulated with a "fairly high content of the ethanolamine to completely emulsify the oil so that it may be removed from the skin by washing with water", i.e. the emulsion is so stable to added water that it is removed by the water without breaking and leaving residual oil on the skin.

The lotion and detergent compositions of U.S. Pat. No. 3,548,056 contain such small quantities (1–3%) of mineral oil that after water rinsing plus drying of the skin, no appreciable quantity of mineral oil would remain to condition and soften the skin. Nowhere in this patent is there any disclosure of skin lotions to be used with rinsing water to produce a beneficial residual effect on the skin.

The waterless skin cleaners of U.S. Pat. No. 3,634,265 are not skin lotions, and are specifically designed to be used without the addition of water. These compositions contain relatively large quantities of liquid isoparaffinic hydrocarbons in addition to mineral oil, resulting in a slippery, oily feel to the compositions when rubbed on the skin. These compositions are solely designed to clean the skin and no residual conditioning effect results or is intended after their removal from the skin.

The lotion compositions of the invention may be prepared according to the following process:

In a suitable mixing vessel containing a high speed mixer, add the water, heat the water to 155° F., and activate the mixer. Then slowly add the thickening agent, if any, to the warm water. When the thickening agent is dispersed evenly in the water, add the $C_{10}$ to $C_{18}$ saturated or monoolefinic fatty acid. When the fatty acid is dissolved or evenly dispersed in the water, add the alkaline neutralizing agent until the desired pH is obtained (pH indicator paper). Then add the $C_{12}$–$C_{15}$ alkali metal alcohol ether sulfate. Next add the mineral oil slowly until a homogeneous emulsion is formed.

The invention is illustrated by the following examples, which are given for illustration purposes only and are not meant to limit the invention.

EXAMPLES

EXAMPLE 1. The following substances are employed:

| Substance | % by weight |
|---|---|
| Water | 71.31 |
| Commercial stearic acid | 2.03 |
| Coconut fatty acid | 0.40 |
| Mixture of $C_{12}$-$C_{15}$ sodium alcohol ether sulfate (Sodium myreth sulfate-SULFOTEX LMSE) | 1.22 |
| Mineral oil, 207 SSU at 100° F. (PRIMOL 205-EXXON) | 23.42 |
| Xanthan gum (KELTROL) | 0.71 |
| Methyl Paraben | 0.15 |
| Propyl Paraben | 0.05 |
| DOWICIL 200 | 0.1 |
| KOH (50% soln. by weight) | 0.61 |
|  | 100.00% |

In a mixing vessel equipped with a high speed mixer, the water is added, heated to 155° F., and the DOWICIL and methyl and propyl Parabens added. The high speed mixer is turned on, and the xanthan gum added slowly to the wall of the resulting vortex until the xanthan gum is uniformly dispersed in the water. The commercial stearic acid and coconut fatty acid is added slowly until solution is achieved. The KOH solution is added, followed by the mineral oil, and the mixing is continued until a uniform emulsion is obtained.

EXAMPLE 2.

The lotion composition of Example 1 is rubbed on the hands, which preferably are premoistened with water, and the hands are then rinsed with water. The hands are then dryed, leaving them clean and non-oily, but with a coat of mineral oil that moisturizes and softens the skin.

EXAMPLE 3.

A lotion composition is formed, using the process set forth in Example 1, containing the following substances:

| Substance | % by weight |
|---|---|
| Water | 71.0 |
| Myristic acid | 2.2 |
| Mixture of $C_{12}$-$C_{15}$ sodium alcohol ether sulfates (AVIROL -BOD 153) | 1.1 |
| Mineral oil, 207 SSU at 100° F. (PRIMOL 205 EXXON) | 24.5 |
| Guar gum | 0.6 |
| Methyl Paraben | 0.2 |
| Triethanolamine | 0.4 |
|  | 100.0% |

What is claimed is:
1. A skin lotion composition for the skin comprising
   (a) from about 55 to about 80 percent by weight of water;
   (b) from about 1.1 to about 5.5 percent by weight of at least one $C_{10}$ to $C_{18}$ saturated or monoolefinic fatty acid;
   (c) from about 15 to about 30 percent by weight of a mineral oil having a viscosity in the range of from about 60 to about 350 SSU at 100° F.;
   (d) from about 0.4 to about 2.0 percent by weight of a $C_{12}$-$C_{15}$ alkali metal alcohol ether sulfate; and

(e) a cosmetically compatible alkaline neutralizing agent in amount sufficient to obtain a pH for the composition in the range of 6.5 to 7.5.

2. A lotion composition as set forth in claim 1 wherein
(a) is from about 65 to about 75 percent by weight;
(b) is from about 1.8 to about 3.0 percent by weight;
(c) is from about 22 to about 25 percent by weight; and
(d) is from about 1.0 to about 1.4 percent by weight.

3. A lotion composition as set forth in claim 2 wherein the composition contains from about 0.01 to about 3.0% of a thickening agent.

4. A skin lotion composition as set forth in claim 2 wherein
(b) is a mixture of USP stearic acid and coconut fatty acids.

5. A lotion composition as set forth in claim 2 wherein (c) is a mineral oil of about 207 SSU viscosity at 100° F.

6. A lotion composition as set forth in claim 2 wherein (d) is a mixture of $C_{12}$–$C_{15}$ sodium alcohol ether sulfates of the formula $C_{12}$–$C_{15}H_{25-31}O(CH_2CH_2O)_2CH_2CH_2OSO_3^-Na^+$.

7. A lotion composition as set forth in claim 2 wherein (e) in claim 1 is KOH.

8. A lotion as set forth in claim 1 wherein
(a) is about 71.3 percent by weight of water;
(b) is about 2.0 percent by weight of USP stearic acid and about 0.4 percent by weight of coconut fatty acids;
(c) is about 23.4 percent by weight of mineral oil of viscosity 207 SSU at 100° F.; (d) is about 1.2 percent by weight of a mixture of $C_{12}$–$C_{15}$ sodium alcohol ether sulfates of the formula $C_{12}$–$C_{15}$ $H_{25-31}O(CH_2CH_2O)_2CH_2CH_2OSO_3^-Na^+$,
wherein the $C_{12}$–$C_{15}$ alkyl groups are predominantly linear alkyl groups;
and the composition contains about 0.7 percent by weight of xanthan gum.

9. A lotion as set forth in claim 8 wherein (e) in claim 1 is about 0.3 percent by weight of KOH.

10. A method of cleansing and conditioning the skin comprising the steps of
(a) applying the skin lotion composition of claim 1 to the skin;
(b) rinsing the skin with water; and
(c) drying the rinsed skin.

* * * * *